(12) United States Patent
Canda

(10) Patent No.: US 10,433,727 B2
(45) Date of Patent: Oct. 8, 2019

(54) METHOD AND MEDICAL DIAGNOSIS COMPUTER FOR DISPLAYING MEDICAL DIAGNOSIS DATA AND/OR INFORMATION ABOUT MEDICAL DIAGNOSIS DATA

(71) Applicant: Siemens Healthcare GmbH, Erlangen (DE)

(72) Inventor: Valer Canda, Erlangen (DE)

(73) Assignee: Siemens Healthcare GmbH, Erlangen (DE)

(*) Notice: Subject to any disclaimer, the term of this patent is extended or adjusted under 35 U.S.C. 154(b) by 0 days.

(21) Appl. No.: 15/720,147

(22) Filed: Sep. 29, 2017

(65) Prior Publication Data
US 2018/0084998 A1 Mar. 29, 2018

(30) Foreign Application Priority Data
Sep. 29, 2016 (DE) .................. 10 2016 218 892

(51) Int. Cl.
| | | |
|---|---|---|
| A61B 5/00 | (2006.01) | |
| G06F 19/00 | (2018.01) | |
| G16H 40/63 | (2018.01) | |
| G16H 50/20 | (2018.01) | |
| A61B 8/00 | (2006.01) | |
| A61B 6/00 | (2006.01) | |

(52) U.S. Cl.
CPC .......... *A61B 5/0035* (2013.01); *A61B 8/463* (2013.01); *G06F 19/32* (2013.01); *G16H 40/63* (2018.01); *G16H 50/20* (2018.01); *A61B 6/463* (2013.01); *A61B 6/501* (2013.01); *A61B 8/466* (2013.01); *G06F 19/34* (2013.01)

(58) Field of Classification Search
CPC combination set(s) only.
See application file for complete search history.

(56) References Cited

U.S. PATENT DOCUMENTS

| | | | | | |
|---|---|---|---|---|---|
| 5,172,103 A | * | 12/1992 | Kita | ................. | G06T 17/00 345/667 |
| 5,469,849 A | * | 11/1995 | Sasaki | ................. | A61B 8/463 600/443 |
| 5,712,995 A | * | 1/1998 | Cohn | ................. | G06F 3/0481 715/792 |

(Continued)

FOREIGN PATENT DOCUMENTS

DE 10332832 A1 10/2004

OTHER PUBLICATIONS

Asbach et al., "Efficient Whole-Body MRI Interpretation: Evaluation of a Dedicated Software Prototype," Journal of Digital Imaging, vol. 21, Suppl .1, pp. S50-S58 (2008).

(Continued)

*Primary Examiner* — Motilewa Good Johnson
(74) *Attorney, Agent, or Firm* — Schiff Hardin LLP (57) ABSTRACT

In a method and computer for displaying medical diagnosis data and/or information about medical diagnosis data at a display screen, an item of information of a displayed content of different categories of medical diagnosis data and/or information about medical diagnosis data is determined in the computer. Using the displayed content, region sizes for display regions, which are respectively associated with one of the different categories are determined, and the display regions are displayed dependent on their region size.

14 Claims, 3 Drawing Sheets

(56) References Cited

U.S. PATENT DOCUMENTS

| | | | | |
|---|---|---|---|---|
| 5,915,240 | A * | 6/1999 | Karpf | G06F 19/324 705/2 |
| 6,008,809 | A * | 12/1999 | Brooks | G06F 3/0481 715/792 |
| 6,322,502 | B1 * | 11/2001 | Schoenberg | G06F 19/3456 600/300 |
| 6,473,088 | B1 * | 10/2002 | Matsumoto | G06F 3/14 345/530 |
| 7,058,901 | B1 * | 6/2006 | Hafey | G16H 40/63 715/792 |
| 7,170,532 | B2 * | 1/2007 | Sako | G06T 7/0012 345/637 |
| 8,520,017 | B2 * | 8/2013 | Kondo | G06F 19/321 345/530 |
| 8,656,302 | B2 * | 2/2014 | Nagano | G06F 3/1454 345/530 |
| 8,743,148 | B2 * | 6/2014 | Gegner | G06F 3/0481 345/660 |
| 8,872,855 | B2 * | 10/2014 | Doll | G09G 5/14 345/649 |
| 9,442,912 | B1 * | 9/2016 | Pearcy | G06F 17/243 |
| 9,836,865 | B2 * | 12/2017 | Dobson | G02B 21/365 |
| 2002/0062068 | A1 * | 5/2002 | Gritzbach | G06Q 50/22 600/300 |
| 2006/0013462 | A1 | 1/2006 | Sadikali | |
| 2009/0016491 | A1 * | 1/2009 | Li | A61B 6/032 378/98.5 |
| 2010/0131890 | A1 | 5/2010 | Natanzon et al. | |
| 2010/0157155 | A1 | 6/2010 | Katsushima | |
| 2013/0222430 | A1 * | 8/2013 | Bredno | G06T 7/0014 345/634 |
| 2015/0065803 | A1 * | 3/2015 | Douglas | A61B 1/00009 600/200 |
| 2015/0310652 | A1 * | 10/2015 | Dobson | G02B 21/365 345/629 |
| 2015/0324093 | A1 * | 11/2015 | Wada | G06F 3/0481 715/763 |
| 2017/0038914 | A1 * | 2/2017 | Kawagishi | G06F 3/0481 |
| 2017/0177096 | A1 * | 6/2017 | Cheong | G06F 1/1641 |
| 2018/0122038 | A1 * | 5/2018 | Wang | G06T 1/20 |

OTHER PUBLICATIONS

Müller-Horvat et al., "Befunderstellung bei der Ganzkörperbildgebung mittels einer workflowoptimierten Befundungssoftware—Erste Erfahrungen einer Multireader-Analyse," Röfo, pp. 721-727 (2007).

* cited by examiner

METHOD AND MEDICAL DIAGNOSIS COMPUTER FOR DISPLAYING MEDICAL DIAGNOSIS DATA AND/OR INFORMATION ABOUT MEDICAL DIAGNOSIS DATA

BACKGROUND OF THE INVENTION

Field of the Invention

The present invention concerns a method for displaying medical diagnosis data and/or information about medical diagnosis data at a display screen of a medical diagnosis computer.

Description of the Prior Art

For diagnoses of medical image data, for example radiological images and/or radiological image data and/or image series, the medical image data have conventionally been displayed in individual image regions or segments of a display screen, wherein the individual image regions or segments each display an image series. If there are no image data available for individual image regions or segments, such as because specific scans were not carried out during a medical imaging examination, in particular a magnetic resonance examination, the corresponding image regions or segments remain empty and are displayed as empty image regions or segments. This leads to ineffective use of the display screen.

SUMMARY OF THE INVENTION

An object of the present invention is to enable effective use of a display screen of a medical diagnosis computer.

The invention includes a method for displaying medical diagnosis data and/or information about medical diagnosis data at a display screen of a medical diagnosis computer, having the following steps:
- providing the computer with at least two different categories of medical diagnosis data and/or information about medical diagnosis data,
- determining, in the computer, an item of information of a displayed content for each of the at least two different categories of medical diagnosis data and/or information about medical diagnosis data,
- providing, in the computer, at least two display regions, wherein one of the at least two display regions respectively is associated with one of the at least two categories of medical diagnosis data and/or information about medical diagnosis data,
- determining a region size in the computer for each of the at least two display regions as a function of the determined information of the displayed content of the associated category of medical diagnosis data and/or information about medical diagnosis data, and
- simultaneously displaying the at least two display regions, which show the medical diagnosis data and/or the information about the medical diagnosis data, on the display screen, with the display being dependent on the region size for the at least two display regions.

The at least two different categories of medical diagnosis data and/or information of medical diagnosis data is/are preferably provided by a control processor of the medical diagnosis computer. Such provision can include, for example, retrieval of medical diagnosis data and/or information about medical diagnosis data from a storage unit. Alternatively or additionally, such provision can also include loading current medical diagnosis data and/or current information about medical diagnosis data which have been acquired by a medical imaging device. In this context, medical diagnosis data means data that allow, or assist in, a diagnosis made by a reporting physician. The medical diagnosis data preferably are medical image data, for example magnetic resonance image data, of a patient. The medical diagnosis data can also include tables containing examination information and/or diagrams and/or text files and/or further displayed contents that are considered expedient to those skilled in the art.

The information about medical diagnosis data can also include tables containing examination information and/or diagrams and/or text files and/or further displayed contents that are considered expedient to those skilled in the art. Furthermore, the information about medical diagnosis data can also include an item of information that no medical diagnosis data exist in this category. A category of medical diagnosis data should, in particular, be taken to mean all medical diagnosis data in which identical parameters exist for acquiring the medical diagnosis data of an examination region of a patient. Furthermore, a category can also include further data and/or information, the information about the acquired data and/or information on the parameter settings and/or information on the patient. Different categories can include, for example t1-images or t2-images or coronal images or images having fat suppression, etc. of an examination region of a patient.

An item of information of a displayed content is similarly preferably determined for each of the at least two different categories of medical diagnosis data and/or information about medical diagnosis data by the control unit of the medical diagnosis computer. The information of the displayed content can include a quantity of data to be displayed of the medical diagnosis data and/or information on the medical diagnosis data which is to be displayed within the display region. Furthermore, the information of the displayed content can include an item of information as to whether medical diagnosis data exist in this category or whether no medical diagnosis data exist in this category.

The display screen has a display area, for example an available display area of a screen and/or a touch display. The available display area of the screen can be, for example, the entire available area of the screen and/or monitor, less further required display elements, such as a task bar and/or a menu bar, etc. For simultaneous displaying of different medical diagnosis data and/or different items of information of medical diagnosis data, the display area is divided into the different display regions. A total of a size of the individual display regions, such as, for example, a size of display windows, should essentially match a size of the display area. The individual display regions can have a predetermined and/or predefined display size and/or region size or also have a display size and/or region size dependent on the displayed content.

An advantage of the invention is that the individual display regions can be variably displayed in respect of their region size as a function of their displayed content. The individual display regions can therefore be displayed for the user and/or reporting physician so as to be dynamically variable, such as if a change and/or deviation in the medical diagnosis data exists, and the display regions can be adapted to the changed diagnosis data. Furthermore, the display area of the display screen can be optimally distributed among the displayed display regions, wherein the region sizes for the individual display regions are preferably also determined as a function of the display area of the display unit. This enables efficient workflow-oriented diagnosis. Furthermore, the display areas are preferably divided automatically and/or spontaneously by the control processor of the diagnosis computer, so manual editing by the user and/or the reporting physician can advantageously be omitted.

In a further embodiment of the invention, for at least one display region, for whose associated category no medical diagnosis data and/or information about medical diagnosis data exists, the at least one display region is not displayed, so displaying of empty display regions can advantageously be prevented. This similarly enables optimum distribution of the display area of the display unit among the display regions to be displayed. Furthermore, an efficient workflow-oriented diagnosis can similarly be achieved since a user and/or reporting physician, for example a doctor, is not distracted by empty display regions.

In another embodiment of the invention, for at least one display region, for whose associated category no medical diagnosis data and/or information about medical diagnosis data exists, a representative element is displayed for the at least one display region for the at least one category of medical diagnosis data and/or information about medical diagnosis data. The representative element can comprise an element, such as, for example, a pictogram element and/or a tooltip, etc. Furthermore, the representative element can be highlighted in color. The representative element preferably requires less space on the display area than the display region. For a user and/or reporting physician this enables information that no data to be displayed exist for this category of medical diagnosis data and/or information about medical diagnosis data to be acquired quickly. Furthermore, this type of information can be displayed particularly compactly for the reporting physician and/or user.

Alternatively or additionally, for at least one display region, for whose associated category no medical diagnosis data and/or information about medical diagnosis data exists, a minimum display region can be displayed for the at least one display region for the at least one category of medical diagnosis data and/or information about medical diagnosis data. The minimum display region can essentially be, for example, two opposing edge regions of the display region and informs the reporting physician and/or user that no data that are to be displayed exist for this category of medical diagnosis data and/or information about medical diagnosis data. Furthermore, the minimum display region can also include a boundary region and/or a boundary line and/or an edge of the display region, with the minimum display region comprising solely the boundary region and/or solely the boundary line and/or solely the edge of the display region. The minimum display region can be encompassed by the representative element. For a user and/or reporting physician this similarly enables information that no data to be displayed exist for this category of medical diagnosis data and/or information about medical diagnosis data to be acquired quickly.

Furthermore, the invention provides for at least one display region, for whose associated category no medical diagnosis data and/or information about medical diagnosis data exists, at least one further display region, for whose associated category medical diagnosis data and/or information about medical diagnosis data does exist, to be displayed with a predefined region size. Therefore, for example display regions of particular categories of medical diagnosis data and/or information about medical diagnosis data can be displayed with the predefined region size. A choice as to which categories of medical diagnosis data and/or information about medical diagnosis data the region size of the respective display region has a predefined region size can also be defined manually by the user and/or the reporting physician. Furthermore, an automatic choice of the categories and/or a default allocation by the system are also possible. In this way simple, user-defined displaying of the individual display regions can be provided for the different categories of medical diagnosis data and/or information from medical diagnosis data. For example, in this way only the display regions of optional categories of medical diagnosis data and/or information from medical diagnosis data can be variably displayed and display region of non-optional categories of medical diagnosis data and/or information from medical diagnosis data can be displayed with a predefined region size.

In a further embodiment of the invention, for at least one display region, for whose associated category no medical diagnosis data and/or information about medical diagnosis data exists, at least one further display region, for whose associated category medical diagnosis data and/or information about medical diagnosis data does exist, is displayed with an adjusted region size. This enables optimum utilization of an available display area of the display unit for the display regions to be displayed during a diagnosis. In particular, the clarity can be improved for the user and/or reporting physician of the display area. The region size is preferably enlarged with the adjustment of the region size of the at least one display region.

The region sizes can be displayed so as to be adjusted for all further display regions. The regions sizes are preferably increased with the adjustment of the region sizes of all further display regions, so a display area available for diagnosis can be optimally used for displaying diagnosis data.

In a further embodiment of the invention, two or more further display regions exist and the two or more further display regions are proportionally displayed based on their region size. This enables particularly simple and effective use of the display area. The region sizes are preferably adjusted spontaneously by the control unit, enabling a particularly convenient diagnosis for the user and/or reporting physician.

In a further embodiment of the invention, at least three display regions, each having an associated category of medical diagnosis data and/or information about medical diagnosis data, can be displayed, wherein for one of the at least three display regions, in whose associated category no medical diagnosis data and/or information about medical diagnosis data exists, wherein a choice of further display regions of the at least three display regions is made and the display regions are displayed with an adjusted region size for this choice of display regions. This enables convenient use of the display area for the user and/or reporting physician. The choice can be only those display regions which directly adjoin the display region, for whose associated category no medical diagnosis data and/or information about medical diagnosis data exists. Alternatively or additionally, the choice can be only those display regions having the smallest region sizes. Further selection criteria that are considered expedient to those skilled in the art can be used. The selection criteria can be adjusted dependent on the user and/or reporting physician.

Furthermore, for at least one display region, a change in the region size can be made as a function of an adjustment and/or a change in a display scale. The change in the display scale is preferably made automatically by the control processor of the display monitor. The change in the display scale can comprise, for example, a zoom function, so the contents of the display region to be displayed are displayed enlarged. The zoom function can comprise, for example, a zoom factor or an adjustable zoom factor. A zoom function of this kind can, moreover, also be determined for two display regions, in particular simultaneously displayed display regions, wherein the two zoom functions and/or zoom factors can be matched to each other. In particular, an adjustable zoom factor can be adjusted to an aspect ratio of the diagnosis data to be displayed and/or to a display region and/or to a display scale. In particular this enables an enlarged display of the medical diagnosis data and/or information about medical diagnosis data, enabling fast acquisition of contents of the display regions for the user and/or reporting physician.

In a further embodiment of the invention, the adjustment and/or change in the display scale can occur as a function of the medical diagnosis data to be displayed and/or the information on the medical diagnosis data to be displayed. For example, the display scale and/or the region size of a display region can be adjusted to an aspect ratio of the medical diagnosis data to be displayed, in particular of medical diagnostic images. This allows the diagnosis data to be displayed with an advantageous clarity for the reporting physician and/or user.

The invention also provides for at least one display region for a category of medical diagnosis data and/or information about medical diagnosis data to be configured by a user in respect of the region size. The user and/or reporting physician can hereby define a region size for individual display regions and/or for individual categories of medical diagnosis data and/or information about medical diagnosis data, such as, for example, a maximum region size for a display region. For example, with a region size defined by the user, an enlargement of the respective display region can be omitted even if a further display region is not displayed due to the insufficiently large region size.

The invention also provides for a region size of a first display region, which is associated with a first category of medical diagnosis data and/or information about medical diagnosis data, and a region size of a second display region, which is associated with a first category of medical diagnosis data and/or information about medical diagnosis data, to be correlated. In this way correlating diagnosis data of different categories can be displayed in display regions with, for example, an identical region size. An adjustment of one of the first or second region sizes of the respective display region could therefore also result in an analogous adjustment of the second or first region size of the respective display region. Display regions that correlate with each other and/or categories of medical diagnosis data and/or information about medical diagnosis data that correlate(s) with each other can comprise, for example, t1-scans or t2-scans of an identical examination region of the patient.

Furthermore, the region sizes of the at least two display regions can be readjusted in the case of a, in terms of time, subsequent and/or renewed provision of at least two different categories of medical diagnosis data and/or information about medical diagnosis data. This enables continuous adjustment of the display regions to current diagnosis data, for example during a continuous scan of a medical imaging examination. In particular, display regions, which have not yet been displayed, due to the existence of new diagnosis data, can be adjusted in their region size and be displayed. For the user and/or reporting physician this appears as an expansion of the respective display region while the remaining displayed display regions do not change size or are displayed in a reduced size. Furthermore, it is also possible that no diagnosis data now exist for individual display regions, which have been displayed previously, and these display regions are no longer displayed therefore.

Furthermore, the invention encompasses a medical diagnosis computer having a display monitor with a screen, and a control processor, wherein the control processor, together with the display screen, are designed to implement the method for displaying medical diagnosis data and/or information about medical diagnosis data as described above. An advantage of the invention is that the individual display regions can be variably displayed in respect of their region size as a function of their displayed content. The individual display regions can therefore be displayed so as to be expandable and/or contractible for the user and/or reporting physician, in particular a doctor, particularly if there is a change in the medical diagnosis data and the display regions are adjusted to the changed diagnosis data. Furthermore, the display area of the display screen can be optimally distributed among the displayed display regions, with the region sizes for the individual display regions preferably also being determined as a function of the display area of the display unit. This enables an efficient workflow-oriented diagnosis, moreover, since a user and/or reporting physician, for example a doctor, can no longer be distracted by empty display regions. Furthermore, the display areas are preferably automatically and/or spontaneously distributed by the control processor of the diagnosis computer, so manual editing by the user and/or the reporting physician can advantageously be omitted.

The advantages of the inventive medical diagnosis computer correspond to the advantages of the inventive method for displaying medical diagnosis data and/or information about medical diagnosis data, and as described above in detail. Features, advantages and alternative embodiments of the method are also applicable to the computer.

The present invention also encompasses a non-transitory, computer-readable data storage medium encoded with programming instructions (program code) that, when the storage medium is loaded into a processor of a medical diagnosis computer, cause the processor and the computer to implement any or all of the embodiments of the method according to the invention, as described above.

DESCRIPTION OF THE PREFERRED EMBODIMENTS

Figure 1:
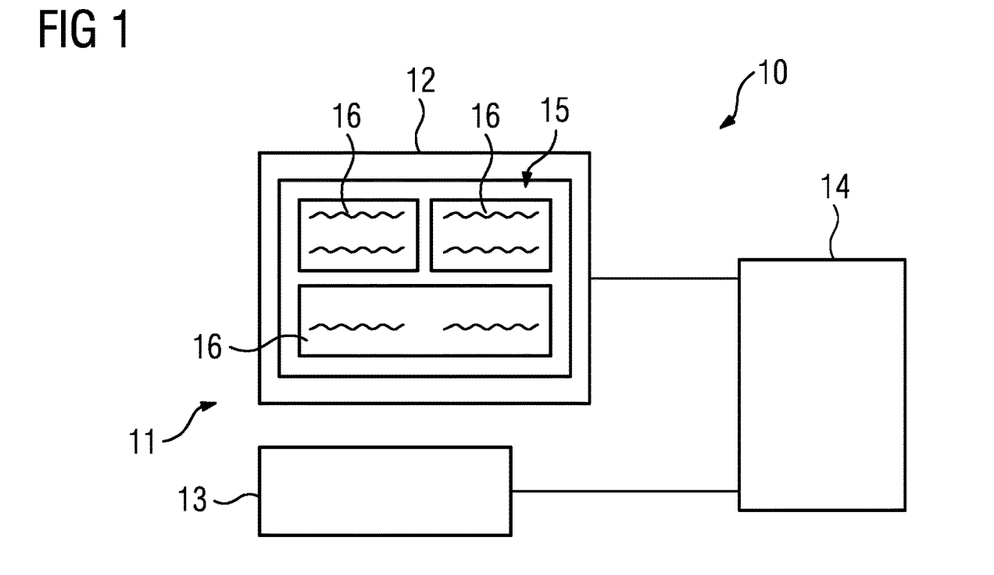
FIG. 1 schematically illustrates an inventive diagnosis computer.

FIG. 1 shows an inventive medical diagnosis computer 10. The medical diagnosis computer 10 comprises a user interface 11 having a display unit 12 and an input unit 13. The input unit 13 can have conventional input elements, such as a keyboard and/or a computer mouse. The display unit 12 has a screen or a touch display, wherein the input unit 13 can already be integrated in the touch display. The display unit 12 has a display area 15 on which information and/or data can be displayed for a user and/or reporting physician. The display area 15 of the display unit 12 is designed for displaying individual display regions 16 which comprise and/or have medical diagnosis data and/or information about medical diagnosis data.

Furthermore, the medical diagnosis computer 10 has a control processor 14. The control processor 14 comprises a core processor (not shown) and a memory (not shown).

Figure 2:
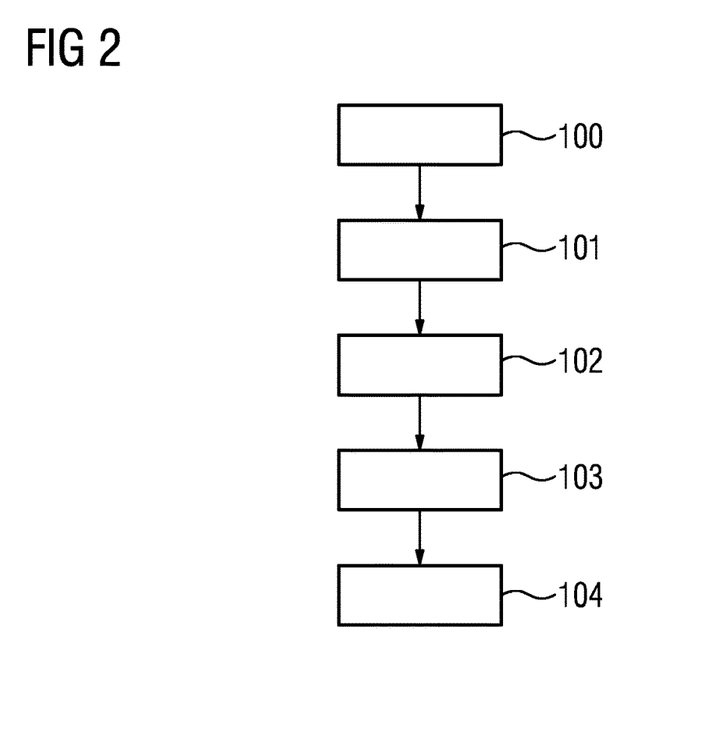
FIG. 2 shows a first exemplary embodiment of the inventive method for displaying medical diagnosis data and/or information about medical diagnosis data.

FIG. 2 shows an inventive method for displaying medical diagnosis data and/or information about medical diagnosis data by the display unit 12. The method is carried out by the control processor 14 together with the display unit 12. For this purpose, the control processor 14 has programs and/or software which carry out a method for displaying medical diagnosis data and/or information about medical diagnosis data when the programs and/or software is/are run in the control processor 14 of the medical diagnosis computer 10. The programs and/or software are stored here in the storage unit of the control processor 14. Furthermore, the different categories of medical diagnosis data and/or an item of information about medical diagnosis data can differ in respect of further parameters.

In a first method step 100, at least two different categories of medical diagnosis data and/or information about medical diagnosis data are provided. The at least two different categories of medical diagnosis data and/or information about medical diagnosis data can differ in respect of at least one recording parameter during data acquisition of the medical diagnosis data on a patient. The medical diagnosis data and/or information about medical diagnosis data can be stored here in the storage unit of the control processor 14 or in an external storage device which is connected to the control processor 14 for the purpose of data exchange. The at least two different categories of medical diagnosis data and/or information about medical diagnosis data are preferably provided automatically and/or spontaneously by the control processor 14.

In a further method step 101, an item of information of a displayed content is determined for each of the at least two different categories of medical diagnosis data and/or information about medical diagnosis data. The information of the displayed content can comprise a quantity of data for display which is to be displayed inside a display region 16. Furthermore, the information of the displayed content can also comprise an item of information as to whether medical diagnosis data exist for display in this category or whether no medical diagnosis data exist for display. The information of a displayed content is preferably determined automatically and/or spontaneously by the control processor 14 for each of the at least one of the at least two different categories of medical diagnosis data and/or information about medical diagnosis data.

In a further method step 102, at least two display regions 16 are provided, wherein one of the at least two categories of medical diagnosis data and/or information about medical diagnosis data is associated with one of the at least two display regions 16 respectively. A display region 16 for displaying the respective medical diagnosis data and/or information about medical diagnosis data is therefore available for each category of medical diagnosis data and/or information about medical diagnosis data. The at least two display regions 16 are preferably provided automatically and/or spontaneously by the control processor 14.

In a further method step 103, a region size is determined for each of the at least two display regions 16. The respective region size is determined here as a function of the determined information of the displayed content of the category of medical diagnosis data and/or information about medical diagnosis data associated with the display region 16. The respective region size is preferably determined as a function of a size of a display area 15 of the display unit 12, so all display regions 16 can be visibly displayed simultaneously for the user and/or reporting physician by the display area 15 of the display unit 16.

The respective region size can be determined automatically and/or spontaneously by the control processor 14. Furthermore, a region size of at least one display region 16 can also be configured in this method step for a category of medical diagnosis data and/or information about medical diagnosis data, in particular for a user and/or reporting physician. The user and/or reporting physician, for example, can define a minimum region size and/or a maximum region size for individual display regions 16 here. Furthermore, the user and/or reporting physician, for example, can define a fixed, unchangeable region size for individual display regions 16 of categories of medical diagnosis data and/or information about medical diagnosis data which is particularly important for diagnosis.

Furthermore, two or more display regions 16 can be correlated with each other. Here, for example, a first region size of a first display region 16, which is associated with a first category of medical diagnosis data and/or information about medical diagnosis data, is correlated with a second region size of a second display region 16, which is associated with a second category of medical diagnosis data and/or information about medical diagnosis data, so the first region size is determined as a function of the determination of the second region size. Similarly, the second region size can be determined as a function of the first region size. The region size defining the two region sizes can be the largest of the two region sizes or the smallest of the two region sizes. For example, two display regions 16 that correlate with each other can be display regions 16 that are adjacent on the display area 15 of the display unit 12. Display regions 16 correlated in this way can, moreover, be displayed for a display as a single display region which comprises the two correlating display regions 16, such as with a single region size. The one region size can depend on a space requirement and/or an available display area.

Display regions 16 that correlate with each other and/or categories of medical diagnosis data and/or information about medical diagnosis data that correlate with each other can comprise, for example, t1-scans or t2-scans of an identical examination region of the patient. In addition, further display regions 16 that correlate with each other and/or categories of medical diagnosis data and/or information about medical diagnosis data that correlate with each other and seem expedient to a person skilled in the art are conceivable. Furthermore, it may also be that a user and/or reporting physician chooses and/or defines at least two display regions 16 that correlate with each other and/or two categories of medical diagnosis data and/or information about medical diagnosis data that correlate with each other.

In a further method step 104, those of the at least two display regions 16, which comprise the medical diagnosis data and/or the information on the medical diagnosis data, are displayed simultaneously on the display area 15 of the display unit 12, if medical diagnosis data and/or information about medical diagnosis data exist for the respectively associated category. This enables a dynamic adjustment of the region size to the determined information of the displayed content for all display regions 16 for which the respectively associated category comprises medical diagnosis data and/or information about medical diagnosis data.

Figure 4:
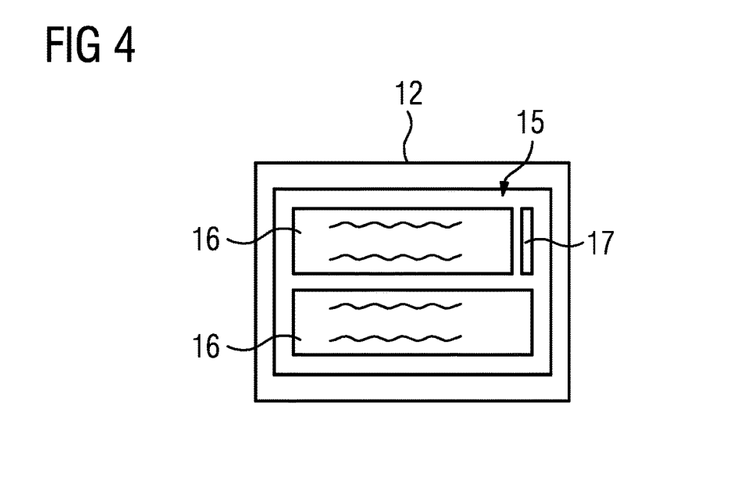
FIG. 4 shows a first exemplary embodiment of a display area with a display of different display regions.
Figure 5:
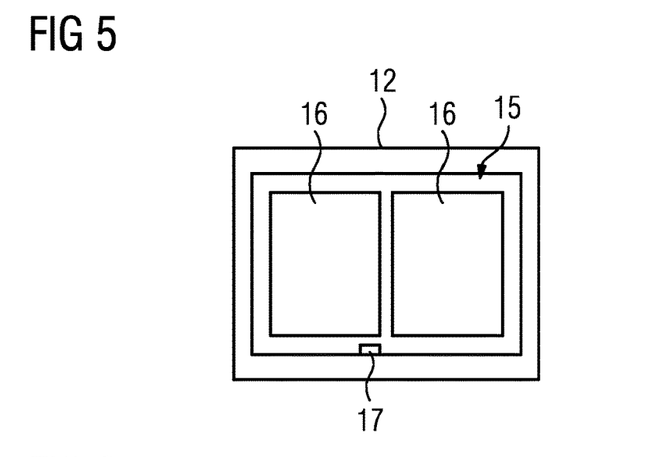
FIG. 5 shows a second exemplary embodiment of a display area with a display of different display regions.

For a display region 16, for whose associated category no medical diagnosis data and/or information about medical diagnosis data exists, displaying of display region 16 can be omitted, so more space is available on the display area 15 for the remaining display regions 16 (FIG. 4 and FIG. 5).

Furthermore, a representative element 17 can be displayed for the display region 16 if for a display region 16, which is associated with a category of medical diagnosis data and/or information about medical diagnosis data, but for whose associated category no medical diagnosis data and/or information about medical diagnosis data exists. The representative element 17 can be an element, such as, for example, a pictogram element and/or a tooltip, etc. Furthermore, the representative element 17 can be highlighted in color. A representative element for a display region 16 can be seen in FIGS. 4 and 5 respectively.

Furthermore, a minimum display region can be displayed for the display region if for a display region 16, which is associated with a category of medical diagnosis data and/or information about medical diagnosis data, but for whose associated category no medical diagnosis data and/or information about medical diagnosis data exist. The minimum display region can be incorporated by the representative element 17, for example the minimum display region can essentially comprise two opposing edge regions of the display region 16 and display to the reporting physician and/or the user that no data to be displayed exist for this category of medical diagnosis data and/or information about medical diagnosis data. Furthermore, the minimum display region can also comprise a boundary region and/or a boundary line and/or an edge of the display region. FIG. 4 shows a representative element 17 as a minimum display region.

Figure 7:
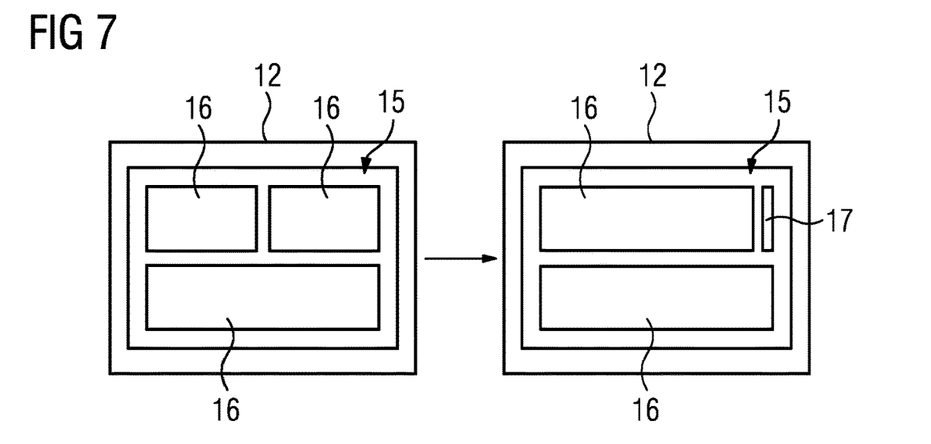
FIG. 7 shows a second exemplary embodiment of a change and/or adjustment in/or individual display regions.

If for a display region 16, which is associated with a category of medical diagnosis data and/or information about medical diagnosis data, but for whose associated category no medical diagnosis data and/or information about medical diagnosis data exist, and consequently the display region 16 is not displayed, then for a further display region 16, for whose associated category medical diagnosis data and/or information about medical diagnosis data does exist, the further display region 16 can be displayed with an adjusted region size in this method step 104. The region size of the further display region 16 can be enlarged, since, due to the display region 16 with the region size for whose associated category no medical diagnosis data and/or information about medical diagnosis data exist not being displayed, a larger region of the display area 15 is available for the further display region 16 (FIGS. 4, 5 and 7). Furthermore, in the event of a display region 16 not being displayed, but for whose associated category no medical diagnosis data and/or information about medical diagnosis data exist, where two or more further display regions 16 exist, for whose associated categories medical diagnosis data and/or information about medical diagnosis data do exist, the further region sizes of the further display regions 16 can be proportionally adjusted based on their region size.

Furthermore, in the case where a display region 16 is not displayed, but for whose associated category no medical diagnosis data and/or information about medical diagnosis data does exist, individual display regions 16, for whose associated categories medical diagnosis data and/or information about medical diagnosis data does exist, can also be unvaryingly displayed or be displayed with a predefined region size. For example, FIG. 7 shows the region size of the lower display region 16 constantly with an unvarying region size. The predefined region size can be specified manually by the user and/or reporting physician, moreover. Furthermore, it is also possible for there to be a choice as to which of the display regions 16 are displayed with an adjusted region size. The choice can be provided by the control processor 14 or be manually defined by the user and/or reporting physician.

Furthermore, it can be provided in this method step 104 that for at least one display region 16 a change in the region size is made as a function of an adjustment and/or a change in a display scale of the display region 16. The change in the display scale can be, for example, a zoom-function, so the contents of the display region 16 to be displayed are displayed enlarged. Alternatively or additionally, the change in the display scale can also be made as a function of the medical diagnosis data and/or information about medical diagnosis data to be displayed.

Figure 3:
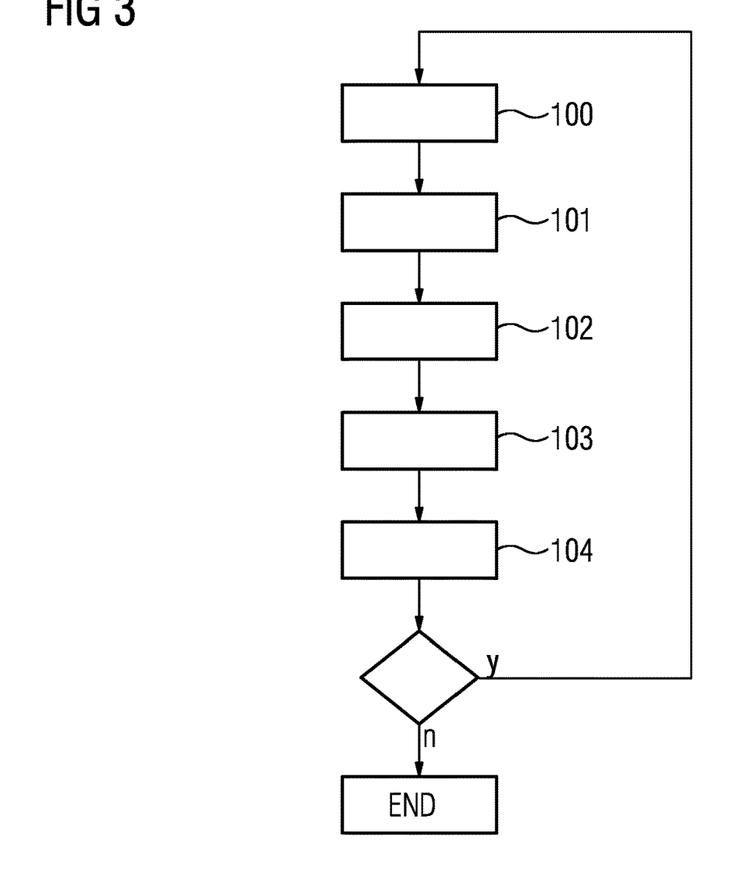
FIG. 3 shows a further exemplary embodiment of the inventive method for displaying medical diagnosis data and/or information about medical diagnosis data.

FIG. 3 shows an alternative exemplary embodiment of the inventive method for displaying medical diagnosis data and/or information about medical diagnosis data. Essentially unchanged components, features and functions are basically provided with identical reference numerals. The description below is essentially limited to the differences from the exemplary embodiment in FIG. 2, with reference being made to the description of the exemplary embodiment in FIG. 2 in respect of unchanged components, features and functions.

The method in FIG. 3 has all method steps 100 to 104 stated in relation to the description of FIG. 2. Compared to the method of FIG. 2, the method in FIG. 3 has an additional method step 200, moreover. In this additional method step 200 a query is made as to whether new and/or additional medical diagnosis data and/or information about medical diagnosis data are available. If new and/or additional medical diagnosis data and/or information about medical diagnosis data are available, the method proceeds through method steps 100 to 104 again. This can lead to new or additional diagnosis data and/or information on diagnosis data existing for individual categories of medical diagnosis data and/or information about medical diagnosis data, and this can lead to a change in the information of the displayed content. Consequently, the individual region sizes of the individual display regions 16 can also be changed and/or adjusted therefore.

Figure 6:
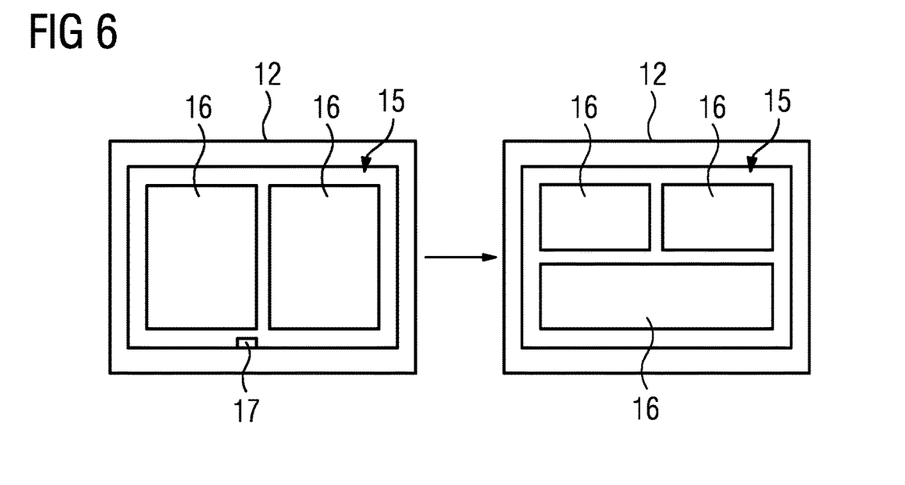
FIG. 6 shows a first exemplary embodiment of a change and/or adjustment in/of individual display regions.

Displaying of the individual display regions 16 is then adjusted in method step 104 to the changed region sizes, as is shown, in particular, in FIGS. 6 and 7. Individual display regions 16, which were previously displayed only by a representative symbol 17, can be displayed with their full region size. This leads to a view of the display area 15 changing for the user and/or reporting physician. The previously displayed display regions 16 reduce in size whereas the display region 16 previously displayed only by the representative symbol enlarges or expands (FIG. 6).

Furthermore, individual, previously displayed display regions 16 can now also be displayed by just a representative symbol 17, so they shrink to the representative symbol 17 in a view of the display area 15. By contrast, the further display regions 16, or at least one of the further display regions 16, can use the region of the display area 15 that has become free and be displayed enlarged (FIG. 7).

FIGS. 4 to 7 show views of the display area 15 having three different display regions 16 and thereby three different categories of medical diagnosis data and/or information about medical diagnosis data. The invention is not limited to three different display regions 16, however, and thereby to three different categories of medical diagnosis data and/or information about medical diagnosis data. The method can also be carried out with more than three different categories of medical diagnosis data and/or information about medical diagnosis data and thereby with more than three different display regions 16. Furthermore, it is also possible for the method to be carried out with just two different categories of medical diagnosis data and/or information about medical diagnosis data and thereby two different display regions 16.

Although modifications and changes may be suggested by those skilled in the art, it is the intention of the Applicant to embody within the patent warranted hereon all changes and modifications as reasonably and properly come within the scope of the Applicant's contribution to the art.

The invention claimed is:

1. A method for displaying a medical diagnosis output comprising at least one of medical diagnosis data and information about medical diagnosis data, at a display screen of a medical diagnosis computer, said method comprising:
   providing said computer with at least two different categories of at least one of said medical diagnosis data and said information about medical diagnosis data in said medical diagnosis output;
   in said computer, determining of displayed content for each of said at least two different categories;
   at said display screen, displaying said displayed content of said at least two different categories in at least two display regions respectively associated with said at least two categories;
   receiving an input into said computer that correlates multiple different categories with each other, among said at least two different categories;
   in said computer, determining a region size for a single display region for said correlated multiple different categories dependent on respective sizes of the display regions for said displayed content of each of said correlated multiple different categories, and changing said display screen to display the display content of all of said correlated multiple different categories in said single region; and
   simultaneously displaying said single display region at said display screen with the determined single region size.

2. A method as claimed in claim 1 comprising, for at least one of said display regions, having a category associated therewith for which no medical diagnosis data or information about medical diagnosis data exists, suppressing display of said at least one display region at said display screen.

3. A method as claimed in claim 1 comprising, for at least one of said display regions having an associated category for which no medical diagnosis data or information about medical diagnosis data exists, displaying a representative element at said display screen for said at least one display region.

4. A method as claimed in claim 1 comprising, for at least one of said display regions having an associated category for which no medical diagnosis data or information about medical diagnosis data exists, displaying a minimum-sized display region at said display screen.

5. A method as claimed in claim 1 comprising, when at least one display region has an associated category for which no medical diagnosis data or information about medical diagnosis data exists, displaying a further display region, having an associated category for which medical diagnosis data or information about medical diagnosis data does exist, at said display screen with a predetermined region size.

6. A method as claimed in claim 1 comprising, when at least one display region has an associated category for which no medical diagnosis data or information about medical diagnosis data exists, displaying a further display region, having an associated category for which medical diagnosis data or information about medical diagnosis data does exist, at said display screen with a adjusted region size.

7. A method as claimed in claim 6 comprising, via said computer, adjusting a size of said adjusted region size so as to cause at least two of said further display region with proportionally adjusted respective region sizes.

8. A method as claimed in claim 6 comprising, in said computer, adjusting said adjusted region size dependent on a change in a display scale for the medical diagnosis data or information about medical diagnosis data in said further display region.

9. A method as claimed in claim 8 comprising changing said display scale dependent on the medical diagnosis data or the information about said medical diagnosis data.

10. A method as claimed in claim 1 comprising displaying at least three display regions at said display screen, with one of said three display regions having an associated category in which no medical diagnosis data or information about medical diagnosis data or information about medical diagnosis data exists, and, in said computer, selecting respective display regions for said at least three display regions with an adjusted region size.

11. A method as claimed in claim 1 comprising allowing manual configuration, via a user interface of said computer, of the region size of at least one of said display regions.

12. A method as claimed in claim 1 comprising readjusting the respective region sizes of at least two said display regions when respective categories are also readjusted.

13. A medical diagnosis computer comprising:
   a processor;
   a display monitor having a display screen in communication with said processor;
   said processor being provided with at least two different categories of at least one of said medical diagnosis data and said information about medical diagnosis data in said medical diagnosis output;
   said processor being configured to determine of displayed content for each of said at least two different categories;
   said processor being configured to display, at said display screen, said displayed content of said at least two different categories in at least two display regions respectively associated with said at least two categories;
   said processor being configured to receive an input that correlates multiple different categories with each other, among said at least two different categories;
   said processor being configured to determine a region size for a single display region for said correlated multiple different categories dependent on respective sizes of the display regions for said displayed content of each of said correlated multiple categories, and changing said display screen to display the display content of all of said correlated multiple different categories in said single region; and
   said processor being configured to simultaneously display said single display region at said display screen with the determined single region size.

14. A non-transitory, computer-readable data storage medium encoded with programming instructions, said storage medium being loaded into a diagnosis computer having a display screen in communication therewith, and said programming instructions causing said computer to:
- designate at least two different categories of at least one of said medical diagnosis data and said information about medical diagnosis data in said medical diagnosis output;
- determine displayed content for each of said at least two different categories;
- at said display screen, display said displayed content of said at least two different categories in at least two display regions respectively associated with said at least two categories;
- receive an input that correlates multiple different categories with each other, among said at least two different categories;
- determine a region size for a single display region for said correlated multiple different categories dependent on said displayed content of said correlated multiple categories, and update said region size for each of said two display regions as said displayed content changes; and
- simultaneously display said single display region at said display screen with the determined single region size.

* * * * *